June 8, 1976
J. W. HINES, Jr.
AZALEA PLANT
Filed Nov. 25, 1974
Plant Pat. 3,901
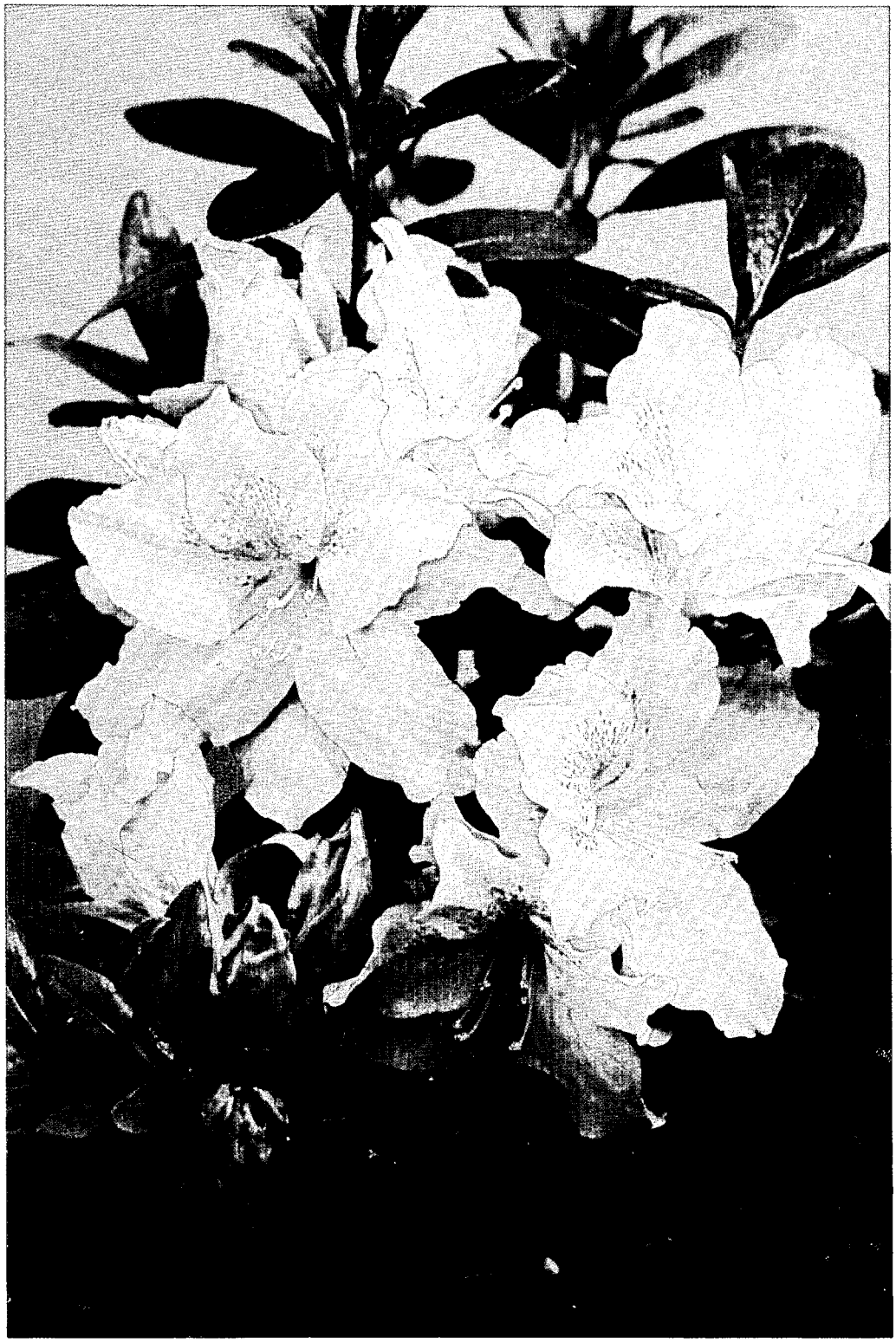

United States Patent

Plant Pat. 3,901

Patented June 8, 1976

3,901

AZALEA PLANT

James W. Hines, Jr., Corona Del Mar, Calif., assignor to Hines Wholesale Nurseries, Santa Ana, Calif.

Filed Nov. 25, 1974, Ser. No. 526,617

Int. Cl. A01h *5/00*

U.S. Cl. Plt.—56 1 Claim

The present invention relates to a new and distinct variety of azalea plant. This plant was originated by me in March 1957, by crossing the azalea variety of the Southern Indica strain, Azalea "Twilight" (unpatented) with the azalea variety of the Belgian Indica strain, Azalea "Twilight"/Azalea "Wm. Van Orange" (unpatented). The seeds which were produced by this hybridization were first sown in September 1957, and the plant first bloomed in March 1958.

As a result of this breeding, I have produced a new and improved azalea variety which is endowed with the following unique combination of characteristics which are outstanding therein, in which distinguish the same from its parents, as well as from all other varieties of which I am aware.

The plant is characterized as to novelty by its ability to grow and flower in full sun or light shade in the southern California area without tip burning of the leaves or blasting of the flowers; by its abundant and rich green foliage and compact and dense habit of growth; by the unique coloring of its flowers; and by its profuse flowering.

The new variety has been asexually reproduced by me on my cultivated property on the Irvine Ranch, near Santa Ana, Calif. Several hundred cuttings of this new and distinct variety have been made since March 1963, and it holds its distinguishing characteristics through succeeding propagations.

The drawings which accompany this petition show a typical view of the flowers and foliage of my new azalea variety. These are portrayed in color as fairly as can possibly be obtained by this method of illustration.

To facilitate identification of the important colors, I have used the color terminology of the R.H.S. Colour Chart issued by the Royal Horticultural Society of London.

Locality where grown and observed: On the Irvine Ranch, approximately 5 miles south of Santa Ana, Calif.

Parentage: Seedling resulting from planned propagation.

*Seed parent.*—Azalea "Twilight" an upatented variety of the Southern Indica strain.

*Pollen parent.*—Azalea "Twilight"/Azalea "Wm. Van Orange," an unpatented variety of the Belgian Indica strain.

THE PLANT

Growth: The plant is of very vigorous growth habit, with dense branching starting just above ground level. Flowering is prolific, with first blooms in late November, and heaviest bloom from late February into March. The plant is suitable for forcing. This plant has a stronger growth habit than the Belgian Indica variety, with plants in the nursery growing to a height of three feet.

Branches: New growth is in the Greyed-Orange Group, Plates 166B to 166C, gradually changing color towards the tip to the Yellow-Green Group, Plates 145A to 145B. Older branches are in the Greyed-Orange Group, Plates 177B to 177C. All branches are hirsute.

Foliage: The leaves are of good substance, semi-glossy and moderately abundant.

Shape: Elliptic with an acute tip. Leaf margins are entire and slightly hairy.

Color:

*New leaves.*—Upper surface and underside are similar in color, both in the Yellow-Green Group, Plates 144A to 144B.

*Mature leaves.*—Upper surface is in the Yellow-Green Group, Plates 146A to 146B. Underside is in the Yellow-Green Group, Plates 147B to 147C.

Size: New leaves range in size from ⅝ to ¾ inches in with, and 1¾ to 2 inches in length. Mature leaves range from ⅞ to 1 inch in width, and 2 and 2½ inches in length.

Veins: Prominent and lighter in color than leaf, running from the petiole to the tip, and having pinnate veins extending therefrom.

THE FLOWER

The plant first flowers in late November, with heaviest bloom in late February, extending to mid-March, with occasional blooming thereafter. The flowers are borne 2 to 6 to a stem, regularly clustered, with flowers appearing at both the tips of the branches and also to mid-branch, creating a very floriferous effect.

Form: Flowers are undulate, hose-in-hose.

Petals: 5 upper petals and 5 lower petals, and at maturity blossoms range in size from 2¾ to 3 inches in width, and a depth of 1¾ to 2 inches.

Color: The color of the flowers are entirely in the Red-Purple Group, with an eye-appealing freshness of color. Colors range in shade from Plates 67A to 67D at the base of the corolla tube, gradually shading to a tone between Plates 63A and 63B and a tone between Plates 62C and 62D toward the petal lobes. The standard and upper wing petals have blotches ranging from a tone between Plates 58A and 58B to a tone between Plates 63A and 63B.

Buds: Long, tapered, and in a range between the Greyed-Purple Group and the Greyed-Red Group, shading from a tone between Plates 186A and 186B to a tone between Plates 179A and 179B.

Reproductive organs: 4 to 6 stamens, with color in the Yellow-Green Group, Plates 149B to 149C. They are from 1 to 1½ inches in length. Pollen is in the Yellow Group, Plates 9B to 9C.

I claim:

1. A new and distinct variety of azalea plant which is a hybrid of the Belgian Indica strain and the Southern Indica strain, and characterized in particular to novelty by its ability to grow and flower in full sun or light shade in the southern California area without tip burning of the leaves or blasting of the flowers; by its moderately abundant and rich green foliage and compact habit of growth; by the unique eye-appealing coloring of its flowers; and by its greater salts tolerance, making it less subject to root diseases common to other varieties grown in the same general area of the Irvine Ranch in southern California.

No references cited.

ROBERT E. BAGWIILL, Primary Examiner